United States Patent [19]

Henry et al.

[11] Patent Number: 5,201,322
[45] Date of Patent: Apr. 13, 1993

[54] DEVICE FOR DETECTING AIR FLOW THROUGH A PASSAGEWAY

[75] Inventors: John C. Henry, Upper Merion; Kyung T. Park, Berwyn, both of Pa.

[73] Assignee: Elf Atochem North America, Inc., Philadelphia, Pa.

[21] Appl. No.: 501,335

[22] Filed: Mar. 28, 1990

Related U.S. Application Data

[63] Continuation of Ser. No. 233,318, Aug. 17, 1988, abandoned.

[51] Int. Cl.⁵ ............................................. A61B 5/08
[52] U.S. Cl. .................................. 128/719; 128/725; 73/861.21; 73/861.52; 73/861.61; 73/DIG. 4; 310/338
[58] Field of Search ............... 128/719, 724, 728, 716, 128/726, 722, 717, 718, 720; 73/861.47, 861.52, 861.61, 861.85, DIG. 4, 861.18, 861.21, 861.24, 31.66, 361.26, 272.12, 198, 195, 158, 189, 861.19, 204.21–204.27; 310/321, 323, 324, 325, 330, 338, 310, 311, 313 R, 315, 317–319, 328, 331, 345, 348, 349, 350, 369; 116/273–275

[56] References Cited

U.S. PATENT DOCUMENTS

| | | |
|---|---|---|
| 3,187,748 | 6/1965 | Mitchell et al. |
| 3,456,644 | 7/1969 | Thiel. |
| 3,456,646 | 7/1969 | Phillips et al. |
| 3,565,070 | 2/1971 | Hanson et al. |
| 3,946,726 | 3/1976 | Pikul ............................ 128/725 |
| 3,962,917 | 6/1976 | Terada ......................... 128/725 |
| 4,100,798 | 7/1978 | Nilsson et al. ............... 310/330 |
| 4,312,235 | 1/1982 | Daigle .......................... 73/861.18 |
| 4,351,192 | 9/1982 | Toda et al. ................... 73/861.18 |
| 4,363,238 | 12/1982 | Willam ........................ 128/724 |
| 4,363,991 | 12/1982 | Edelman. |
| 4,393,884 | 7/1983 | Jacobs. |
| 4,536,674 | 8/1985 | Schmidt. |
| 4,585,970 | 4/1986 | Koal et al. |
| 4,596,153 | 6/1986 | Macdonald et al. .......... 310/330 |
| 4,600,855 | 7/1986 | Strachan ....................... 310/338 |
| 4,607,254 | 8/1986 | Carlson ......................... 73/861.18 |
| 4,648,393 | 3/1987 | Landis et al. |
| 4,802,485 | 2/1989 | Bowers et al. ............... 128/670 |
| 4,841,938 | 6/1989 | Weibler et al. ............... 73/204.21 |

FOREIGN PATENT DOCUMENTS

| | | |
|---|---|---|
| 0314325 | 10/1988 | European Pat. Off. |
| 1466810 | 1/1969 | Fed. Rep. of Germany ...... 128/716 |
| 2928808 | 1/1981 | Fed. Rep. of Germany ... 73/861.21 |
| 0150147 | 8/1981 | Fed. Rep. of Germany ...... 128/716 |
| 3529367 | 2/1987 | German Democratic Rep. ......................... 128/725 |
| 0040820 | 2/1988 | Japan .......................... 73/861.19 |
| 1299571 | 3/1987 | U.S.S.R. ..................... 128/725 |
| 2121185 | 12/1983 | United Kingdom ........ 128/725 |
| 2220485 | 1/1990 | United Kingdom. |

*Primary Examiner*—Randall L. Green
*Assistant Examiner*—K. Reichle
*Attorney, Agent, or Firm*—Panitch Schwarze Jacobs & Nadel

[57] ABSTRACT

A device is disclosed for detecting the presence and direction of air flow through a passageway having a first opening and a second opening for air to flow therethrough in either a first direction or a second direction. The device comprises a piezoelectric sensor located within the passageway. A flow director is provided within the passageway for directing air flow through the passageway for impingement upon the sensor. The sensor generates a first electrical signal when air flows through the passageway in the first direction and a second electrical signal when air flows through the passageway in the second direction. A discriminator is electrically connected to the sensor for receiving the first and second electrical signals and for discriminating between the two signals to identify the direction of air flow through the passageway.

8 Claims, 5 Drawing Sheets

DEVICE FOR DETECTING AIR FLOW THROUGH A PASSAGEWAY

This is a continuation of U.S. patent application Ser. No. 233,318, filed Aug. 17, 1988, now abandoned.

BACKGROUND OF THE INVENTION

The present invention relates generally to a device for detecting air flow through a passageway and, more particularly, to such a device which detects the presence of air flow, as well as the direction and magnitude of air flow through such a passageway.

The present invention, in one embodiment, is suitable for use in an inhalation device for the delivery of fluid or medication to a user. Small hand-held inhalation devices are widely used for dispensing or administering prescribed dosages of aerosol-type medication, particularly for persons having breathing disorders, such as asthma or the like. Such dispensing devices generally comprise a plastic, generally tubular housing which is generally L-shaped in cross section. One end of the housing is adapted for receiving an aerosol container or module which contains the medication, as well as some form of propellant. The other end of the housing includes a mouthpiece which is adapted to be inserted into the mouth of the user. The housing also includes some type of actuating device which causes the medication to be released from the aerosol module for inhalation by the user. Typically, release of the medication requires that the module be moved inwardly with respect to the housing for release of the medication.

As previously indicated, inhalation devices of the type described above are widely used for the delivery of such medication. However, many persons are unable to successfully utilize such devices. Devices of this type generally require that the aerosol module be moved with respect to the housing to release the medication into the housing essentially simultaneously with or immediately followed by inhalation to obtain the full benefit of the medication. Many patients, because of infirmities, age or the like are unable to successfully perform such a two-step process, either simultaneously or in rapid succession. Consequently, such persons either cannot utilize such inhalation devices at all or, in some cases, obtain only a partial benefit from the medication.

The present invention is employed as part of an automatic inhalation device which requires only a single action on the part of the user: inhalation. Means are provided for detecting inhalation by the user and for automatically actuating the aerosol module for release of a predetermined quantity or dose of the medication without any further action by the user.

In another embodiment, the present invention may be employed for monitoring the breathing of a user. For example, the present invention may be employed with a trachea tube or a mouth- or nose-inserted breathing tube for monitoring the breathing of the user. The present invention permits monitoring of the respiration rate and the depth of breath, as well as changes in the respiration rate.

SUMMARY OF THE INVENTION

Briefly stated, the present invention comprises a device for detecting air flow through a passageway having a first opening and a second opening for air to flow therethrough, either in a first direction in which air flows into the first opening and out of the second opening, or in a second direction in which air flows into the second opening and out of the first opening. The device comprises a piezoelectric sensor located within the passageway. Flow directing means within the passageway are provided for directing air flow through the passageway for impingement upon the sensor. The sensor generates a first electrical signal when air flows through the passageway in the first direction and a second electrical signal when air flow through the passageway in the second direction. Discriminating means, electrically connected to the sensor, are provided for receiving the first and second electrical signals and for discriminating between the two signals to identify the direction of air flow through the passageway.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, the embodiments which are presently preferred are shown in the drawings. It is understood, however, that this invention is not limited to the precise arrangements and instrumentalities shown. In the drawings.

DESCRIPTION OF PREFERRED EMBODIMENT

Figure 1:
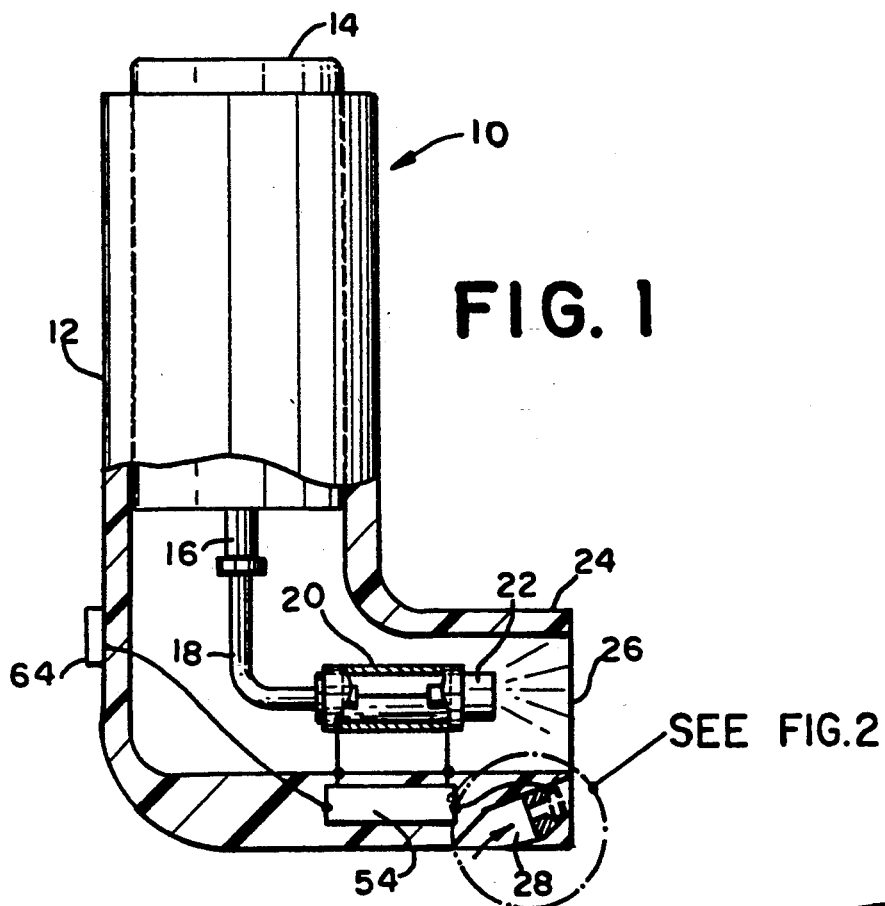
FIG. 1 is a side elevation view, partially broken away, of an inhalation device in accordance with the present invention.

Referring in detail to the drawings, wherein like numerals indicate like elements throughout, there is shown in FIG. 1 a side elevational view, partially broken away, of a preferred embodiment of an automatic inhalation device 10 made in accordance with the present invention. The inhalation device 10 includes a generally tubular housing 12 which is similar in size and shape to inhalation devices presently available. As shown in FIG. 1, the housing 12 is generally L-shaped in cross section. Preferably, the housing 12 is made of a lightweight, high strength plastic material of the type employed to make the inhalation devices presently available. However, it will be appreciated by those skilled in the art that the housing could be made of any other suitable material and that the housing could be of any other size and/or shape.

The housing 12 includes means for receiving and engaging an aerosol container or module 14 containing a fluid or medication to be dispensed under pressure. Aerosol modules of this type are generally well known in the art and are available from a variety of sources. Such aerosol modules generally contain a predetermined amount of a prescribed or other medication, along with a suitable propellant, usually a gas. These aerosol modules generally include some type of valve, usually a depressible valve, which is adapted to release the fluid or medication when depressed by a user. Such aerosol modules are generally cylindrical in shape but may vary in diameter and/or length, depending upon the amount of the fluid or medication contained therein. In the presently preferred embodiment, the housing 12 is generally tubular, with the inside diameter or at least a portion of the housing walls which surround the aerosol module 14 being at least slightly greater than the outside diameter of the aerosol module 14 to permit the free passage of air therethrough. In this manner, the aerosol module 14 may be conveniently inserted in the usual manner by the user into the housing 12 to the position as shown in FIG. 1. Thus, as with the presently used inhalers, when the fluid from an aerosol module 14 has been completely disposed, the aerosol module 14 may be conveniently removed from the housing 12 and replaced with a new, filled aerosol module, permitting the inhalation device 10 to be employed with a series of different aerosol modules.

In the presently preferred embodiment of the invention, the valve 16 of the aerosol module 14 is adapted for insertion into one end of a generally tubular L-shaped conduit 18. A portion of the aerosol module 14 is tightly engaged by the housing 12 to hold the aerosol module in place and to depress the valve 16 and maintain the valve 16 in an open condition when inserted into conduit 18, as shown, so that the pressurized fluid flows into the conduit 18. The other end of the conduit 18 is secured to one end of a low power mechanical actuator means. In the presently preferred embodiment, the actuator means is comprised of a valve 20 formed with a shape memory alloy fiber. Valves of this type are generally well known in the art and are commercially available from Tokiamerica Technologies, of Irvine, Calif., and are sold under the trademark "BIOMETAL." A complete description of the structure and operation of such valves is available from the manufacturer and is not necessary for a complete understanding of the present invention. Suffice it to say that such valves are generally tubular and generally include a single fiber of a shape metal alloy, such as titanium-nickel. Such fibers have a diameter in the range of 6 mils and, due to their structure, act like a human muscle upon activation. Passing a small current, on the order of approximately 300 milliamperes through the fiber at a low voltage, on the order of 1.5 volts causes the fiber to contract, thereby opening the valve. Once the current flow through the fiber ceases, the fiber relaxes or expands to its original position, thereby closing the valve. A discharge opening 22 is provided on the other end of the valve 20. In this manner, the valve 20 essentially takes the place of valve 16 and actuation of the valve 20 results in a discharge of the fluid from the aerosol module 14 into the housing 12. It will be appreciated by those skilled in the art that while a "BIOMETAL" valve is presently preferred, any other type of lightweight, low power mechanical or electromechanical actuator could alternatively be employed.

The housing 12 also includes a mouthpiece 24 for engagement by the mouth of the user in the same manner as inhalation devices currently employed. The mouthpiece includes a mouthpiece opening 26 proximate the valve discharge opening 22. In this manner, when the mouth of a user is placed over the mouthpiece 24, inhalation by the user draws air through the housing 12 (around the aerosol module 14) and into the mouth of the user through the mouthpiece opening 26, thereby resulting in inhalation of any fluid or medication discharged into the housing through the valve discharge opening 22.

The housing 12 also includes a small sized, generally cylindrical passageway 28 which, in the presently preferred embodiment, is disposed within a lower portion of the housing 12 proximate the mouthpiece 24. It will be appreciated by those skilled in the art that the passageway 28 may alternatively be at some other location within the housing 12. A first end 30 of the passageway 28 is open to the atmosphere at a point beyond the area over which the mouth of the user is placed for the entry of air. The second end 32 of the passageway 28 communicates with the mouthpiece opening 26. In this manner, when the mouth of the user is placed over the mouthpiece 24 and the user inhales, a small portion of the inhaled air flows through the passageway 28, as indicated by flow arrow 34.

Detecting means are provided within the passageway 28 for detecting inhalation of the user through the mouthpiece opening 26 and for generating an electrical signal in response thereto. In the presently preferred embodiment, the detecting means comprises a piezoelectric sensor 36. The piezoelectric sensor 36 is preferably formed of an electrode coated thin layer of piezoelectric polymer film of a type commercially available from Pennwalt Corporation, of Philadelphia, Pa., as KYNAR ® piezo film. The sensor 36 also includes a pair of electrical leads which are connected to control means in a manner which will hereinafter become apparent. The sensor 36 could be formed of some other type of piezoelectric or any other suitable material, either in film form or some other form.

In the presently preferred embodiment, the piezoelectric film sensor 36 detects inhalation based upon the presence of air flow through passageway 28. Alternatively, the sensor 36 could be employed for the detection of temperature changes in the air flowing through the passageway, i.e., warmer air from exhalation by the user and cooler air from inhalation by the user.

The piezoelectric film sensor 36 is located within a generally cup-shaped cavity 38 formed within passageway 28 by a first air flow restrictor 40 generally facing the first passageway end 30 and a second air flow restrictor 42 generally facing the second passageway end 32. The first and second air flow restrictors 40 and 42 are preferably formed of the same material employed for forming the housing 12. Alternatively, the first and second air flow restrictors 40 and 42 may be formed of any other suitable material. In the presently preferred embodiment, the first and second air flow restrictors 40 and 42 are generally annular to define generally circular first and second openings 44 and 46, respectively, generally centered within passageway 28. In this manner, the first and second restrictors 40 and 42 function as flow directing means for directing the flow of air through the passageway 28 for impingement upon the sensor 36. However, it will be appreciated by those skilled in the art that the air flow restrictors 40 and 42 need not be annular and that the 44 and 46 need not be circular or centered within the passageway 28. In the presently preferred embodiment, a generally circular opening 48 also extends through the piezoelectric film sensor 36. Again, the sensor opening 48 could be of some shape other than circular, if desired.

Figure 2:
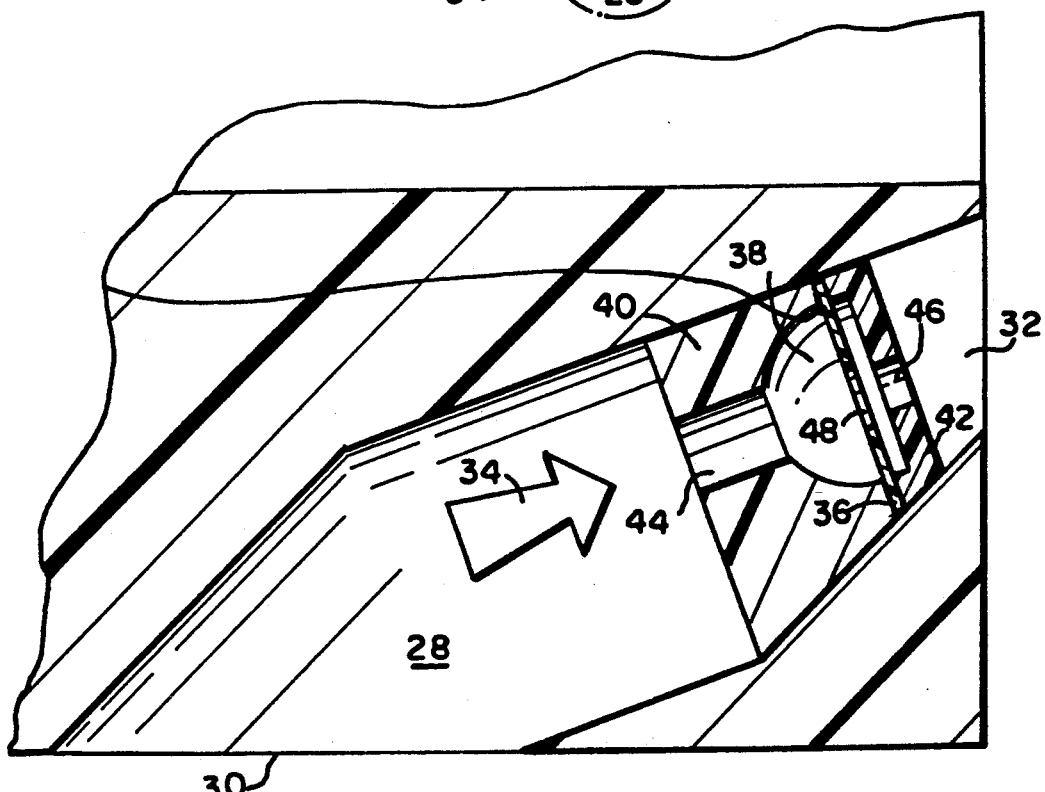
FIG. 2 is a greatly enlarged sectional view of a portion of the device shown in FIG. 1.

As best seen in FIG. 2, the first circular opening 44 is of a diameter greater than the diameter of the second circular opening 46. Similarly, the diameter of the sensor opening 48 is preferably at least slightly greater than the diameter of the second circular opening 46. It should also be noted that the piezoelectric film sensor 36 is positioned within the cavity 38 proximate the second air flow restrictor 42. The purpose in mounting the piezoelectric film sensor 36 in the cavity 38 in this manner and in providing the openings 44, 46 and 48 with varying diameters in this manner is to permit identification of the direction of air flow through the passageway 28 based upon the degree of vibration of the piezoelectric film 36. Air flowing through the passageway 28 in the direction indicated by flow arrow 34 (inhalation by the user) has a greater degree of impact force upon the piezoelectric film sensor 36, due to the relatively large size of circular opening 44 in conjunction with cavity 38, causing a relatively higher degree of vibration of the sensor 36. Inhalation by the user thereby results in the generation of relatively large amplitude electrical signals by the piezoelectric film sensor 36, indicated as 50 on FIG. 5. Alternatively, air flow in the direction opposite that of flow arrow 34 (exhalation by the user) impacts upon a relatively small area of the piezoelectric film sensor 36, due to the relatively small size of circular opening 46, resulting in a relatively lower degree of vibration of the sensor 36 and the generation of relatively small amplitude electrical signals by the piezoelectric film sensor 36, as indicated by 52 on FIG. 5. By discriminating between the large amplitude signals (inhalation) and the small amplitude signals (exhalation) generated by the piezoelectric film sensor 36, the present invention causes the fluid from the aerosol module 14 to be discharged into the housing 12 only at the proper time (inhalation) in a manner which will hereinafter be described in greater detail.

The inhalation device 10 further includes control means 54 within the housing 12 and electrically connected to the detecting means or piezoelectric film sensor 36 for receiving an air flow electrical signal from the detecting means and for generating an actuating signal in response thereto. The control means 54 is also electrically connected to the actuator means or valve 20 for sending the actuating signal to the actuator means or valve 20 to actuate or open the valve. In the presently preferred embodiment, the control means 54 is preferably located within the lower end of the housing 12 (see FIG. 1) proximate the valve 20. However, the control means 54 could be positioned at any other suitable location within the housing 12.

Figure 3:
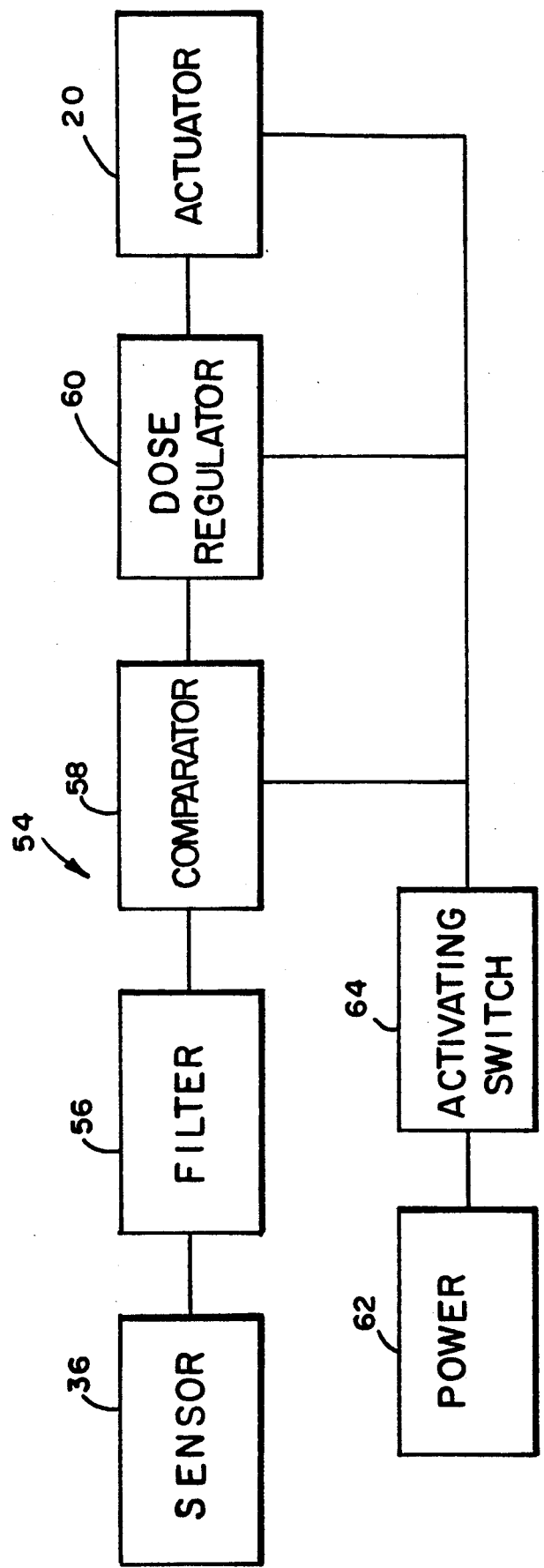
FIG. 3 is a schematic functional block diagram illustrating the operation of the device shown in FIG. 1.

FIG. 3 shows a schematic functional block diagram of a presently preferred manner of implementing the control means 54. Preferably, the air flow electrical signal from the piezoelectric film sensor 36 is initially applied to a first discriminating device, such as a filter 56. In the presently preferred embodiment, the filter 56 is a high pass filter which filters out undesired low frequency signals from the sensor 36. Such low frequency signals may be generated as a result of thermal or other noise and/or vibrations and are not indicative of the activity which the sensor 36 is employed to detect, i.e., inhalation. The filtered signal from the sensor 36 is then applied to a second discriminating device, such as a comparator 58, which compares the amplitude of the filtered signal to a predetermined reference. The predetermined reference is established to be of an amplitude greater than the level of signals generated by the piezoelectric film sensor 36 during exhalation of the user, as indicated at 52 on FIG. 5. Upon receipt of a signal having an amplitude greater than the predetermined reference, the comparator 58 instantaneously generates an electrical trigger signal which is applied to a dose regulator 60. The dose regulator 60 operates as a timing device and, once activated by the trigger signal from the comparator 58, generates an actuating signal having a predetermined time length corresponding to the time necessary to open the valve 20 for delivering the desired quantity or dose of fluid or medication from the aerosol module 14 into the housing 12. The length of the actuating signal may be varied, depending upon the particular type of fluid or medication being delivered and depending upon the needs of the particular user.

The control means 54 also includes a power source 62. In the presently preferred embodiment, the power source 62 is comprised of a small sized one and one-half volt battery of the type commonly employed in hearing aids or watches, but could be some other power source such as a solar cell. Electrical power from the power source 62 is applied to the other components of the control means 54 through an activating switch 64. In the presently preferred embodiment, the activating switch 64 is comprised of a small push button type switch, which is located on the housing 12, proximate the control means 54. However, it will be appreciated by those skilled in the art that the activating switch 64 may comprise any other suitable type of switch, such as a slide switch and may be located at any other suitable position within the housing 12. The purpose of the activating switch 64 is to serve as a safety device to prevent inadvertent actuation of the aerosol module 14, thereby preventing undesired loss of the fluid or medication.

Figure 4:
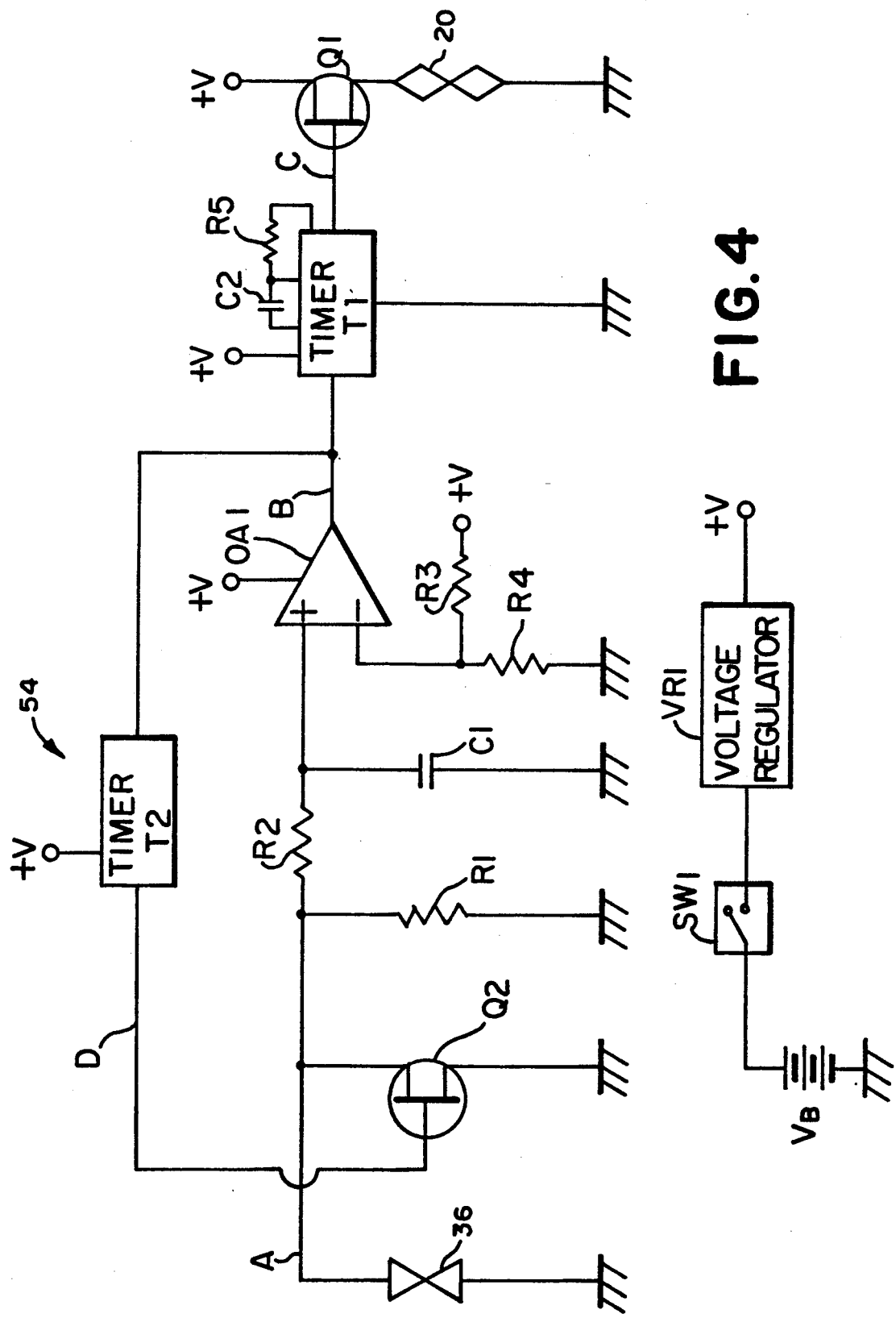
FIG. 4 is a circuit diagram illustrating a preferred manner of implementing the schematic block diagram of FIG. 3.

FIG. 4 is a circuit diagram of a presently preferred electrical circuit for implementing the schematic functional block diagram of FIG. 3. The circuitry shown in FIG. 4 is comprised primarily of discrete components. It will be appreciate by those skilled in the art that other types of discrete components may alternatively be employed for implementing the same functions. It will also be appreciated by those skilled in the art that the same functions may alternatively be achieved utilizing some other type of electronics such as a custom or semi-custom integrated circuit or chip in a manner well known in the art.

Referring to FIG. 4, it can be seen that the function of the high pass filter 56 is implemented utilizing a standard RC filter comprised of resistor R2 and capacitor C1, the values of which are determined by the frequencies desired to be passed and/or eliminated. Resistor R1 serves as a stabilizing resistor.

The function of the comparator 58 is implemented by operational amplifier OA1, which receives the output of the R2-C1 filter at its positive input terminal. The negative input terminal of operational amplifier OA1 is connected to a voltage divider formed by resistors R3 and R4 to establish the predetermined reference or threshold voltage. The values for resistors R3 and R4 are selected to provide a reference or threshold voltage which is greater than the maximum amplitude of the electrical signals generated by the piezoelectric film sensor 36 during user exhalation. Upon receipt of an inhalation signal at its positive input terminal which exceeds the reference or threshold voltage at its negative input terminal (shown at A on FIG. 5), the operational amplifier OA1 generates an output trigger signal in the form of a small positive voltage pulse, indicated at on the timing diagram of FIG. 5.

The output trigger signal from operational amplifier OA1 is applied to the input terminal of a first timer T1. In the presently preferred embodiment, the timer T1 is a "4538" timer or one-shot. Alternatively, a "555" timer may be employed. Both of these devices are of a type well known in the art and commercially available. Other timers or related components or circuitry may alternatively be employed. The timer T1 performs the function of the dose regulator 60 and generates an actuating signal shown as C on the timing diagram of FIG. 5, having a time duration corresponding to a first, predetermined time period. The duration of the actuating signal is established by the time constant of the RC circuit formed by resistor R5 and capacitor C2. As previously indicated, the time constant of timer T1 may be altered to vary the amount or dose of the fluid or medication discharged into the housing 12, depending upon the characteristics of the particular medication and/or fluid (i.e., strength) and/or characteristics of the user.

The actuating signal from the timer T1 is applied to the gate terminal of a field effect transistor (FET) Q1 or some other type of switching transistor or device. Upon application of the actuating signal, the FET Q1 becomes conductive, thereby permitting the flow of current through the actuator or valve 20 to open the valve 20 for the duration of the activating signal and to thereby discharge the predetermined quantity of fluid or medication into the housing 12. Once the R5-C2 timing circuit has timed out, the actuating signal from timer T1 ends, and the FET Q1 again becomes non-conductive, stopping the flow of current through the valve 20 to close the valve 20 and stop the discharge of the fluid or medication into the housing 12.

Figure 5:
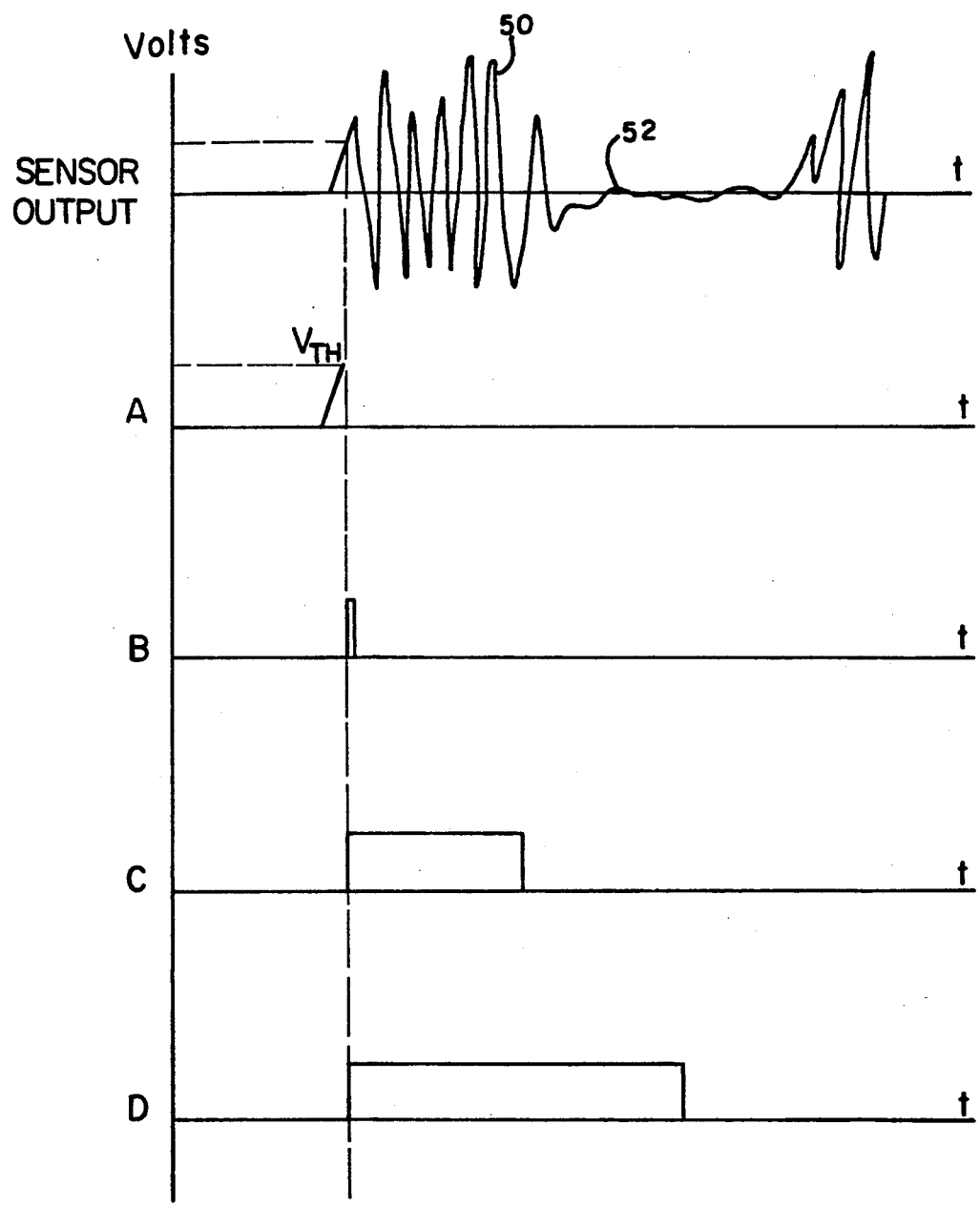
FIG. 5 is a timing diagram containing representative signals generated in conjunction with the operation of the circuitry of FIG. 4.

A second timer T2, also preferably a "4538" timer, but, alternatively, some other timer or similar circuit, also receives the trigger signal from the operational amplifier OA1 and generates a positive output signal shown as D on the timing diagram of FIG. 5. The output signal of timer T2 is applied to the gate of a second field effect transistor FET Q2 or some other switching transistor or device, which, in turn, is connected between the input to the R2-C1 filter and ground. When FET Q2 becomes conductive upon receipt of the signal from timer T2, further signals from the piezoelectric film sensor 36 are grounded through FET Q2 and, therefore, are not applied to operational amplifier OA1. In this manner, generation of a second actuating signal by the operational amplifier OA1 and timer T1 is prevented for a second predetermined time period corresponding to the length of the signal of line D in the timing diagram of FIG. 5. Since the second predetermined time period is greater than the first predetermined time period (C on FIG. 5), inadvertent subsequent actuation of the aerosol module 14 by a long inhalation or a series of short inhalations is prevented.

The functioning of the power source 62 and activating switch 64 is illustrated in FIG. 4 by batteries VB, switch SW1 and voltage regulator VR1. All of these components are of a type well known in the art.

To use the inhalation device 10, a user initially installs an aerosol module 14 containing the desired fluid or medication into the housing 12 to the position shown in FIG. 1. The mouthpiece 24 is then placed within the mouth of the user and the activating switch 64 is depressed. As previously discussed, depressing the activating switch 64 completes the circuit to provide power to, and thus to enable, the control means 54. Thereafter, the user inhales, thereby drawing air into the housing 12 around the aerosol module 14 and through passageway 28 in the direction of flow arrow 34. The air flowing through passageway 28 causes piezoelectric film sensor 36 to vibrate, as previously described, thereby generating an air flow electrical signal 50. If the air flow electrical signal exceeds the reference or threshold signal (indicating inhalation), an actuating signal (C) of a first predetermined time length is generated and is used to apply a current through the shape metal valve 20. The application of the actuating signal causes the shape metal valve 20 to open for the first predetermined time period, causing the aerosol module 14 to discharge a predetermined amount of fluid or medication into the housing 12, proximate the mouthpiece opening 26. Inhalation by the user draws additional air into the housing, both through the passageway 28 and around the aerosol module 14 to convey the discharged fluid or medication into the mouth and subsequently into the lungs of the user.

After the expiration of the first predetermined time period (C), when the proper amount of fluid or medication has been discharged and inhaled by the user, continued inhalation by the user does not result in further actuation of the aerosol module 14 because of the second timer T2. When the user has received the fluid or medication, the activating switch 64 is released to remove power from, and/or disable, the control means 54, to thereby preclude further actuation of the aerosol module 14.

Figure 6:
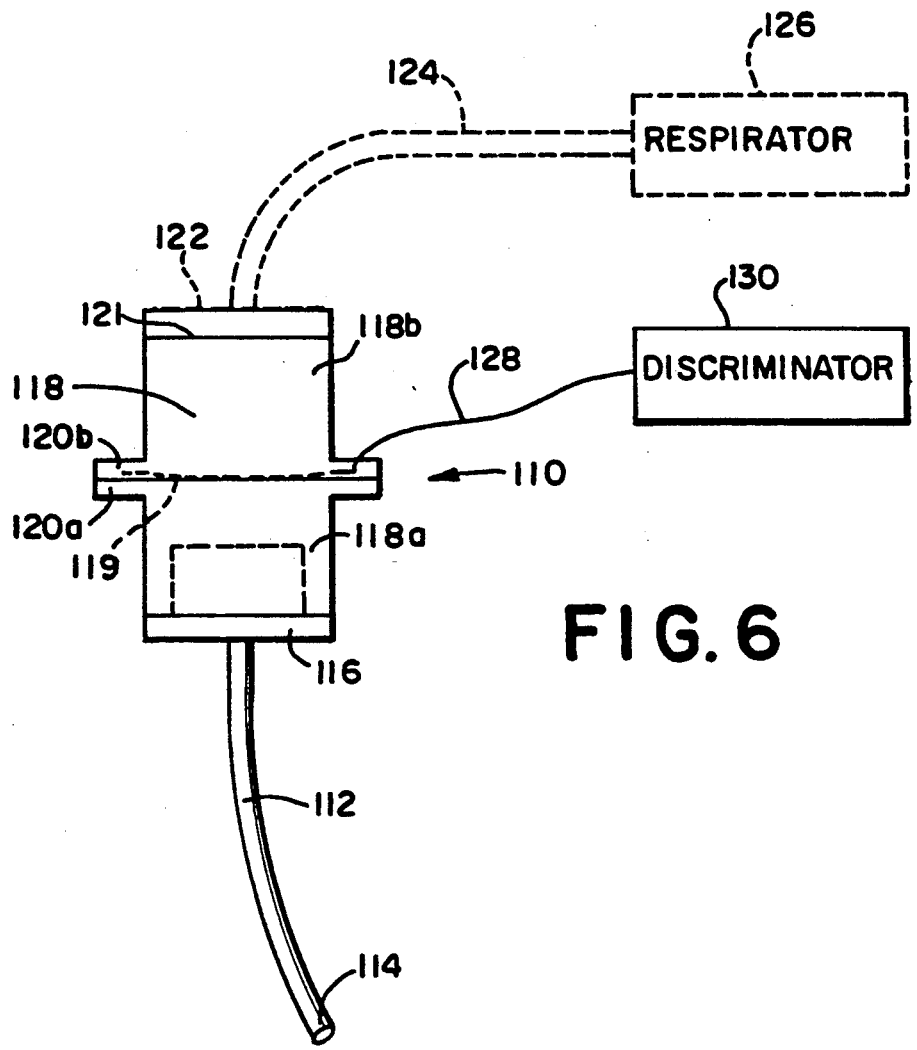
FIG. 6 is a side elevational view of a breathing tube illustrating an alternate embodiment of the present invention.

Referring now to FIG. 6, there is shown a breathing tube apparatus 110 in accordance with the present invention. The apparatus 110 includes a generally flexible tubular member 112 having a free or unconnected end 114, which is adapted to be inserted into the mouth or nose of a user in a manner well known in the art. The other end of the flexible tubular member 112 is secured to a generally cylindrical connector member 116, which is also of a type generally well known in the art. The connector member 116 is removably secured to one end of a generally cylindrical housing 118, which is formed of two engaged subhousings 118a and 118b secured together by a pair of generally annular flange members 120a and 120b. A second connector member shown in phantom as 122 may be employed for providing communication via a second flexible tubular member 124 to a respirator shown in phantom as 126. Alternatively, the other or distal end 121 of the housing 118 may remain unattached, as shown in solid lines in FIG. 6.

A generally cylindrical passageway (not shown in FIG. 6), which is substantially the same as passageway 28, extends generally through the housing 118 in substantially the same manner as shown in FIG. 2. The passageway has a first opening proximate the distal end 121 of the housing 118 and a second opening proximate connector member 116. Housing 118 also includes first and second restrictors (not shown) and a piezoelectric film sensor, shown in phantom at 119, which are secured within the passageway of housing 118 in substantially the same manner as the corresponding components shown in FIG. 2. Suitable electrical wires or leads 128 extend from the piezoelectric film sensor 119 within housing 118 to electronic circuitry in the form of a discriminator 130. In the presently preferred embodiment, the flexible tubular member 112, as well as the connector member 116 and the housing 118, are preferably formed of plastic materials of the type well known in the art and generally employed for fabricating such components. However, these components could be formed of other materials suitable for the intended purposes, as will hereinafter become apparent.

One particular use for the apparatus 110 is for detecting the direction of air flow into and out of the lungs of a user. In this use, the flexible tubular member 112 is installed into the mouth or nose of the user. Alternatively, the housing 118 could be connected to the distal end of a trachea tube (not shown) utilizing a suitable connector member. The end 121 of the housing 118 remote from the connector 116 is generally open to the atmosphere, thereby forming a first opening to the passageway, substantially the same as opening 30 of FIG. 2. Similarly, the second opening within the passageway communicates with the connector member 116, and, through the tubular member 112, communicates with the respiratory system of the user. In this manner, inhalation by the user causes air to flow into the passageway through the first opening and out of the passageway through the second opening. Correspondingly, exhalation by the user causes air to flow into the passageway through the second opening and out of the passageway through the first opening. As described in detail above with respect to FIG. 2, the two restrictors (not shown on FIG. 6) form flow directing means for directing the flow of air through the passageway of housing 118 for impingement upon the piezoelectric film sensor 119. As with the piezoelectric film sensor described in conjunction with FIG. 2, piezoelectric film sensor 119 generates a first electrical signal upon inhalation of the user and a second electrical signal upon exhalation of the user. Examples of signals of this type are indicated on FIG. 5 by reference numerals 50 and 52, respectively.

Figure 7:
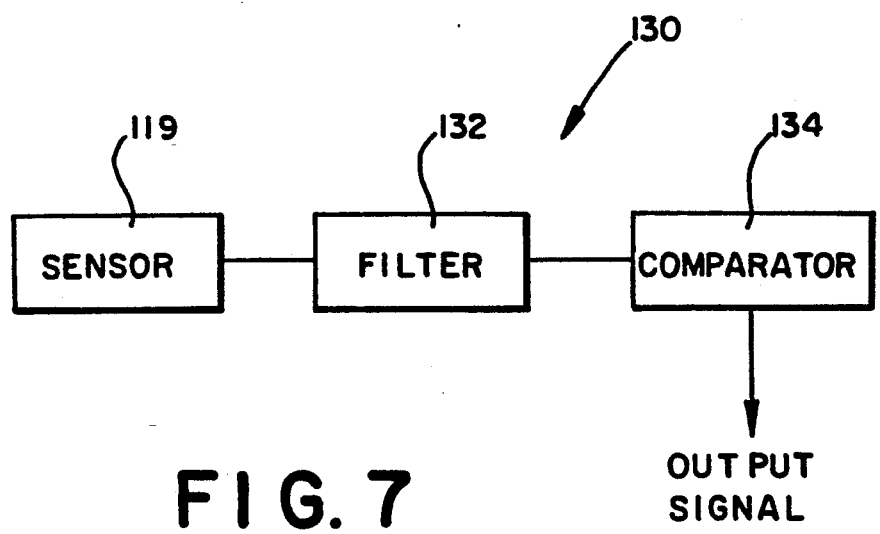
FIG. 7 is a schematic functional block diagram illustrating employment of the device shown in FIG. 6.

The signals from the sensor 119 are received by the discriminator 130 along leads 128. The discriminator discriminates or differentiates between the two electrical signals to identify inhalation and exhalation of the user. FIG. 7 shows a functional, schematic block diagram of the discriminator 130. The discriminator 130 includes a filter 132, which is employed for filtering out noise and other unwanted signals received from the sensor 119. The filtered sensor signals are then applied to a comparator 134, which compares the signals to one or more fixed references. The comparator generates an output signal to indicate the presence of an air flow resulting from inhalation or an air flow resulting from exhalation. The discriminator 130 may be implemented by a person skilled in the art utilizing circuitry similar to the control means 54 as shown in FIG. 4 and described in detail above. Alternatively, the discriminator may be implemented utilizing other components and/or integrated circuitry.

The output signal from the comparator 134 may be utilized to monitor various aspects of the breathing of the user. For example, the output signal may be fed to a counter or other such accumulating device (not shown) which may then count or calculate the respiration rate of the user. The respiration rate may then be visually displayed utilizing a known display device for immediate use by a doctor, nurse, paramedic or other person for analysis of the breathing condition of the user. Alternatively, the respiration rate may be continuously recorded on a chart or any other suitable storage medium for subsequent review and analysis of the user's respiration rate over a long period of time. The respiration rate may also be electronically compared to one or more preset limits for triggering an audible or other alarm if any of the limits are exceeded.

The output signal from the comparator 134 may also be employed for determining the depth of breath of the user or magnitude of the air flowing into and out of the lungs of the user. It will be appreciated that the amplitude of the electrical signals generated by the piezoelectric sensor 119 are proportional to the volume flow rate of the air flowing through the passageway. Similarly, the duration of the generated signals is proportional to the duration of inhalation or exhalation by the user. The amplitude and duration of the output signals from the comparator 134 similarly correspond to air flow volume flow rate and duration. By knowing the size or cross sectional area of the passageway and the various openings through the passageway in conjunction with the volume flow rate and duration of the inhalation or exhalation signals, the depth of breath of the user can be determined, utilizing calculating techniques known in the art. In addition, suitable circuitry (not shown) can be developed for automatically calculating depth of breath of the user for a particular apparatus 110, after suitable calibration.

Another use for the present invention is to detect the presence of air flow through the passageway. In this manner, a breathing tube 110, or other such device, may be employed for detecting whether or not the user is breathing. Thus, in the absence of an output signal from the comparator 134 for a predetermined period time, a respirator 126 could be actuated to provide breathing assistance to a user, as required.

From the foregoing description, it can be seen that the present invention comprises a device for detecting the presence and/or direction of air flow through a passageway. It will be appreciated by those skilled in the art that changes may be made to the above-described embodiments of the invention without departing from the broad inventive concepts thereof. It is understood, therefore, that this invention is not limited to the particular embodiments disclosed, but is intended to cover all modifications which are within the scope and spirit of the invention as defined by the appended claims.

We claim:

1. A device for detecting the direction of air flow through a passageway comprising:
   a passageway having a first opening and a second opening for air to flow therethrough either in a first direction in which air flows into the first opening and out of the second opening, or in a second direction in which air flows into the second opening and out of the first opening;
   a piezoelectric sensor positioned within the passageway such that air flowing through the passageway impinges upon the sensor and causes the sensor to vibrate, the sensor generating different electrical signals in accordance with a degree of vibration;
   a first restrictor within the passageway facing the first opening for directing air flowing through the passageway in the first direction to impact the sensor with a first force to thereby cause the sensor to have a first degree of vibration and a second restrictor within the passageway facing the second opening for directing air flowing through the passageway in the second direction to impact the sensor with a second force to thereby cause the sensor to have a second degree of vibration, the sensor being located between the first and second restrictors and generating a first electrical signal in response to the first degree of vibration and a second electrical signal in response to the second degree of vibration; and discriminating means electrically connected to the sensor for receiving the first and second electrical signals from the sensor and for discriminating between the two signals to identify the direction of air flow through the passageway.

2. The device as recited in claim 1 wherein the first electrical signal has an amplitude which is greater than the amplitude of the second electrical signal, the discriminating means discriminating between the two signals by comparing the amplitude of the two signals to a predetermined reference.

3. The device as recited in claim 1 wherein the first restrictor forms an opening of a first predetermined area and the second restrictor forms an opening of a second predetermined area, the first predetermined area being greater than the second predetermined area.

4. A device for detecting the direction of air flow through the respiratory system of a user comprising:

a passageway having a first opening and a second opening, the second opening for communicating with the respiratory system of the user, whereby when the second opening communicates with the respiratory system of the user, inhalation by the user causes air to flow in a first direction into the passageway through the first opening and out of the passageway through the second opening, and exhalation by the user causes air to flow in a second direction into the passageway through the second opening and out of the passageway through the first opening;

a piezoelectric sensor positioned within the passageway such that air flowing through the passageway impinges upon the sensor and causes the sensor to vibrate, the sensor generating different electrical signals in accordance with a degree of vibration;

a first restrictor within the passageway facing the first opening for directing air flowing through the passageway in the first direction to impact the sensor with a first force to thereby cause the sensor to have a first degree of vibration and a second restrictor within the passageway facing the second opening for directing air flowing through the passageway in the second direction to impact the sensor with a second force to thereby cause the sensor to have a second degree of vibration, the sensor being located between the first and second restrictors and generating a first electrical signal in response to the first degree of vibration and a second electrical signal in response to the second degree of vibration; and discriminating means electrically connected to the sensor for receiving the first and second electrical signals from the sensor and for discriminating between the two signals to identify the air flow direction.

5. The device as recited in claim 4 wherein the first electrical signal has an amplitude which is greater than the amplitude of the second electrical signal, the discriminating means discriminating between the two signals by comparing the amplitude of the two signals to a predetermined reference.

6. The device as recited in claim 4 wherein the first restrictor forms an opening of a first predetermined area and the second restrictor forms an opening of a second predetermined area, the first predetermined area being greater than the second predetermined area.

7. A device for detecting the magnitude of air flow through the respiratory system of a user comprising:

a passageway having a first opening and a second opening and a predetermined cross-sectional area, the second opening for communicating with the respiratory system of the user, whereby when the second opening communicates with the respiratory system inhalation by the user causes air to flow in a first direction into the passageway through the first opening and out of the passageway through the second opening, and exhalation by the user causes air to flow in a second direction into the passageway through the second opening and out of the passageway through the first opening;

a piezoelectric sensor positioned within the passageway such that air flowing through the passageway impinges upon the sensor and causes the sensor to vibrate, the sensor generating different electrical signals in accordance with a degree of vibration;

flow directing means located within the passageway for directing air flowing through the passageway in the first direction to impact the sensor with a first force to thereby cause the sensor to have a first degree of vibration and for directing air flowing through the passageway in the second direction to impact the sensor with a second force to thereby cause the sensor to have a second degree of vibration, the sensor generating a first electrical signal in response to the first degree of vibration and a second electrical signal in response to the second degree of vibration; and pulse generating means connected to the sensor for receiving the generated electrical signals from the sensor and for generating a digital output signal comprising a digital pulse having a pulse height proportional to the volume flow rate of the air flow through the passageway and having a pulse width corresponding to the duration of the air flow through the passageway; and means for receiving the digital output signal from the pulse generating means and utilizing the cross-sectional area of the passageway therewith for determining the magnitude of air flowing through the passageway.

8. A device for detecting the presence of air flow through a passageway comprising:

a passageway having a first opening and a second opening for air to flow therethrough either in a first direction in which air flows into the first opening and out of the second opening, or in a second direction in which air flows into the second opening and out of the first opening;

a piezoelectric sensor positioned within the passageway such that air flowing through the passageway impinges upon the sensor and causes the sensor to vibrate, the sensor generating different electrical signals in accordance with a degree of vibration; and a first restrictor within the passageway facing the first opening directing air flowing through the passageway in the first direction to impact the sensor with a first force to thereby cause the sensor to have a first degree of vibration and a second restrictor within the passageway facing the second opening for directing air flowing through the passageway in the second direction to impact the sensor with a second force to thereby cause the sensor to have a second degree of vibration, the sensor being located between the first and second restrictors and generating a first electrical signal in response to the first degree of vibration and a second electrical signal in response to the second degree of vibration.

* * * * *